(12) United States Patent
Madelmont et al.

(10) Patent No.: US 6,759,406 B1
(45) Date of Patent: Jul. 6, 2004

(54) QUATERNARY AMMONIUM COMPOUNDS

(75) Inventors: Jean-Claude Madelmont, Romagnat (FR); Isabelle Giraud, Dourdan (FR); Colette Nicolas, Le Cheix-sur-Morge (FR); Jean-Claude Maurizis, Perignat-les-Sarlieve (FR); Maryse Rapp, Veyre-Monton (FR); Monique Ollier, Romagnat (FR); Pierre Renard, Le Chesney (FR); Daniel-Henri Caignard, Le Pecq (FR)

(73) Assignees: Les Laboratoires Servier, Courbevoie Cedex (FR); INSERM, Paris Cedex (FR)

( * ) Notice: Subject to any disclaimer, the term of this patent is extended or adjusted under 35 U.S.C. 154(b) by 57 days.

(21) Appl. No.: 10/019,804

(22) PCT Filed: Jun. 22, 2000

(86) PCT No.: PCT/FR00/01731

§ 371 (c)(1),
(2), (4) Date: Mar. 25, 2002

(87) PCT Pub. No.: WO01/00621

PCT Pub. Date: Jan. 4, 2001

(30) Foreign Application Priority Data

Jun. 23, 1999 (FR) .............................. 99 08020

(51) Int. Cl.⁷ ..................... C07D 409/06; A61P 19/00
(52) U.S. Cl. ..................... 514/226.5; 544/49
(58) Field of Search .......................... 514/226.5; 544/49

(56) References Cited

PUBLICATIONS

Reymond et al. (Helvicta Chimica Acta—vol. 79 (1996), 1651–1669).*

\* cited by examiner

*Primary Examiner*—Bruck Kifle
(74) *Attorney, Agent, or Firm*—The Firm of Hueschen and Sage

(57) ABSTRACT

Compounds of formula corresponding to either formula (Ia) or (Ib):

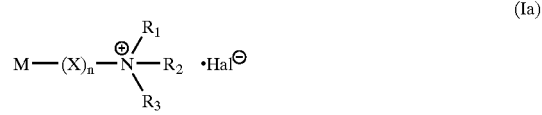

(Ia)

wherein:
M represents a molecule that can be used for the treatment or diagnosis of pathologies caused by attack on the cartilage,
$R_1$, $R_2$ and $R_3$ represent an alkyl group, or $R_1$, $R_2$ and $R_3$, together with the nitrogen atom carrying them, form a heterocycle,
X represents a $(C_1-C_6)$alkylene chain in which one or more $-CH_2-$ groups are optionally replaced by a sulphur atom, an oxygen atom, or an $-NR-$, $-CO-$, $-CO-NH-$, $-CO_2-$, $-SO-$ or $-SO_2-$ group,
n represents 0 or 1,
Hal represents a halogen atom,
or,

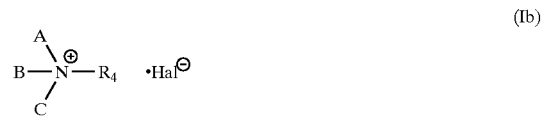
(Ib)

$R_4$ represents an alkyl group,
Hal represents a halogen atom,

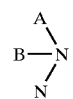

represents a molecule that can be used for the treatment or diagnosis of pathologies caused by attack on the cartilage, wherein the nitrogen atom may optionally be included in a saturated or unsaturated nitrogen-containing heterocyclic system, or included in a double bond; and pharmaceutical compositions thereof.

3 Claims, No Drawings

QUATERNARY AMMONIUM COMPOUNDS

FIELD OF THE INVENTION

The present invention relates to new quaternary ammonium compounds and to pharmaceutical compositions containing them.

DESCRIPTION OF THE INVENTION

The new quaternary ammonium compounds enable the vectorisation of active ingredients in cartilaginous tissue and hence the treatment of pathologies caused by attack on the cartilage whether they are articular or cancerous pathologies. They may also be used as diagnostic reagents, capable, for example, of revealing a pathology of the cartilage or a metabolism (radioactive marker, stained marker, . . . ).

The therapeutic agents currently available commercially for the treatment of articular pathologies, such as arthritis or osteoarthritis, generally exhibit a low affinity for the target tissues and require the administration of high doses to achieve the desired therapeutic effect.

The administration of such strong doses of active ingredients gives rise to an increase in the frequency of side effects. For example, the administration of non-steroidal anti-inflammatories is known to cause significant digestive toxicity.

In the field of bone cancerology, the therapeutic agents currently used for the treatment of chondrosarcomas are likewise known, for example, to produce undesirable side effects, especially toxicities, for example haematological or non-haematological toxicities.

Finally, in the field of diagnostic products for cartilaginous pathologies, the products currently used have the disadvantage of lacking specificity for the targets at which they are aimed.

There has thus been particular interest in functionalising those different kinds of compound in order specifically to target cartilaginous tissue and thus limit, or even suppress, the undesirable effects observed when such compounds are administered directly.

The new compounds forming the subject of the present invention make it possible, both by increasing the tropism and by decreasing the doses administered, for the side effects to be significantly attenuated and for the therapeutic index of the active molecules to be strengthened.

DETAILED DESCRIPTION OF THE INVENTION

The present invention relates more specifically to compounds of a formula corresponding to formula (Ia) or (Ib):

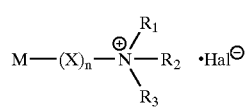

(Ia)

wherein:

M represents a molecule that can be used for the treatment or diagnosis of pathologies caused by attack on the cartilage, $R_1$, $R_2$ and $R_3$, which may be identical or different, represent a linear or branched ($C_1$–$C_6$)alkyl group, or $R_1$, $R_2$ and $R_3$, together with the nitrogen atom carrying them, form a saturated or unsaturated nitrogen-containing heterocycle, X represents a linear or branched ($C_1$–$C_6$)alkylene chain in which one or more —$CH_2$-groups are optionally replaced by a sulphur atom, an oxygen atom, an —NR— group (wherein R represents a linear or branched ($C_1$–$C_6$)alkyl group), a —CO— group, a —CO—NH— group, a —$CO_2$— group, an —SO— group or an —$SO_2$— group, n represents 0 or 1, and Hal represents a halogen atom, or,

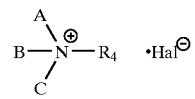

(Ib)

$R_4$ represents a linear or branched ($C_1$–$C_6$)alkyl group,

Hal represents a halogen atom, and

represents a molecule that can be used for the treatment or diagnosis of pathologies caused by attack on the cartilage, wherein the nitrogen atom may optionally be included in a saturated or unsaturated nitrogen-containing heterocyclic system, or included in a double bond.

Preferably, the compounds of formula (Ia) are compounds wherein:

n is 1,

X represents a linear or branched ($C_1$–$C_6$)alkylene chain, a group —NR—$(CH_2)_m$— (wherein R is as defined hereinbefore), a group —CO—$(CH_2)_m$—, or a group —CO—NH—$(CH_2)_m$, in which groups m represents an integer from 1 to 5 inclusive.

$R_1$, $R_2$ and $R_3$ in the compounds of formula (Ia) are preferably identical or different, linear or branched ($C_1$–$C_6$)alkyl groups or, together with the nitrogen atom carrying them, form a pyridine or piperidine ring (in which case one of those groups is a linear or branched ($C_1$–$C_6$)alkyl group).

The molecules M or

that can be used for the treatment or the diagnosis of pathologies caused by attack on the cartilage are more especially: antiinflammatories, antiarthritics, antiosteoarthritics, analgesics or specific anti-tumour agents.

Preferred compounds of formula (Ia) used as active ingredient are:

molecules derived from tenidap of formula (Ia$_1$):

(Ia$_1$)

wherein:

$X_1$ represents a linear or branched ($C_1$–$C_6$)alkylene group, $R'_1$, $R'_2$ and $R'_3$, which may be identical or different, represent a linear or branched ($C_1$–$C_6$)alkyl group, and Hal represents a halogen atom, molecules derived from melphalan of formula (Ia$_2$):

(Ia$_2$)

wherein:

$X_2$ represents a group —NH—(CH$_2$)$_m$— wherein m is as defined hereinbefore, $R'_1$, $R'_2$ and $R'_3$ are as defined hereinbefore, and Hal represents a halogen atom, molecules derived from chlorambucil of formula (Ia$_3$);

(Ia$_3$)

wherein:

$X_2$, $R'_1$, $R'_2$ and $R'_3$ are as defined hereinbefore, and

Hal represents a halogen atom, molecules derived from glucosamine of formula (Ia$_4$):

(Ia$_4$)

wherein:

$X_4$ represents a group —CO—(CH$_2$)$_m$— wherein m is as defined hereinbefore, $R_1$, $R_2$ and $R_3$ are as defined hereinbefore, and Hal represents a halogen atom.

Preferred compounds of formula (Ib) used as active ingredient are:

molecules derived from piroxicam of formula (Ib$_1$):

(Ib$_1$)

wherein $R_4$ and Hal are as defined hereinbefore, molecules of formula (Ib$_2$):

(Ib$_2$)

wherein $R_4$ and Hal are as defined hereinbefore.

Preferred compounds of formula (Ia) used as diagnostic reagents are compounds of formula (Ia$_5$):

(Ia$_5$)

wherein $X_1$, $R_1$, $R_2$, $R_3$ and Hal are as defined hereinbefore.

The invention relates also to a process for the preparation of the compounds of formula (Ia) or (Ib).

The compounds of formula (Ia) are obtained according to conventional processes of organic chemistry by functionalisation in one or more steps, according to the nature of the X group required, of a compound of formula M—P (wherein M is as defined for formula (Ia) and P represents a hydrogen atom or a hydroxy group) or of a precursor of the compound of formula M—P followed by the reactions necessary for the formation of the final compound of formula (Ia).

The compounds of formula (Ib) are obtained by reaction of an alkyl halide with a compound of formula

as defined hereinbefore.

The molecules derived from tenidap of formula (Ia$_1$) defined hereinbefore are obtained starting from 4-nitrophenyl 5-chloro-2,3-dihydro-2-oxo-1H-indole-1-carboxylate, which is reacted with an amine of formula (II):

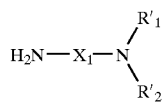
(II)

wherein $X_1$, $R'_1$ and $R'_2$ are as defined hereinbefore, to yield a compound of formula (III):

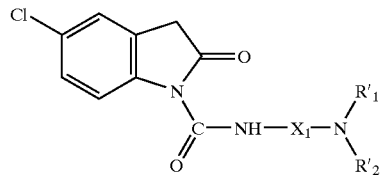
(III)

wherein $X_1$, $R'_1$ and $R'_2$ are as defined hereinbefore, which is subjected to the action of 2-thenoyl chloride in basic medium, under an inert atmosphere, and then to treatment with an acid, to yield a compound of formula (IV):

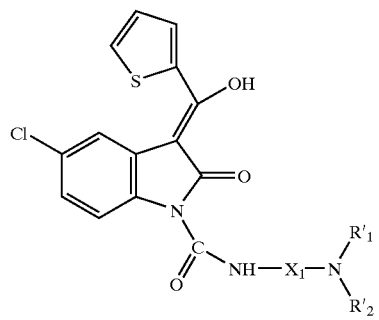
(IV)

which is converted into the corresponding sodium salt, which is then subjected to the action of a linear or branched ($C_1$–$C_6$)alkyl halide ($R'_3$Hal) to yield a compound of formula (V):

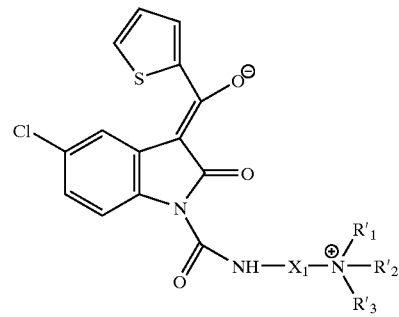
(V)

which, in hydrochloric medium, yields a compound of formula (Ia$_1$), which if necessary is purified.

The molecules derived from melphalan of formula (Ia$_2$) defined hereinbefore are obtained starting from melphalan, the amine function of which has been protected beforehand by a tert-butoxycarbonyl group (Boc), using an amine of formula (VI) in the presence of a peptide coupling reagent:

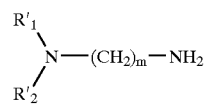
(VI)

wherein $R'_1$, $R'_2$ and m are as defined hereinbefore, to yield a compound of (VII):

(VII)

Cl—(CH$_2$)$_2$\
        N—⟨C$_6$H$_4$⟩—CH(CH$_2$NHBoc)—CO—NH—(CH$_2$)$_m$—N(R'$_1$)(R'$_2$)\
Cl—(CH$_2$)$_2$/ wherein m, $R'_1$ and $R'_2$ are as defined hereinbefore, which is subjected to the action of a linear or branched ($C_1$–$C_6$)alkyl halide, then to treatment with HCl, to yield a compound of formula (Ia$_2$), which if necessary is purified.

The molecules derived from chlorambucil of formula (Ia$_3$) defined hereinbefore are obtained starting from chlorambucil, the acid function of which is converted into the corresponding acid chloride, which is then reacted with an amine of formula (VI), in the presence or absence of a peptide coupling reagent:

(VI)

$R'_1$\
  N—(CH$_2$)$_m$—NH$_2$\
$R'_2$/ wherein R'$_1$, R'$_2$ and m are as defined hereinbefore, a to yield a compound of formula (VIII):

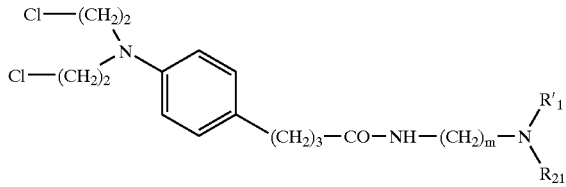
(VIII)

wherein m, R'$_1$ and R'$_2$ are as defined hereinbefore, which is subjected to the action of a linear or branched (C$_1$–C$_6$)alkyl halide, to yield a compound of formula (Ia$_2$), which if necessary is purified.

The molecules derived from glucosamine of formula (Ia$_4$) defined hereinbefore are obtained by reaction of glucosamine with an acid chloride of formula (IX):

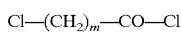
(IX)

to yield a compound of formula (X):

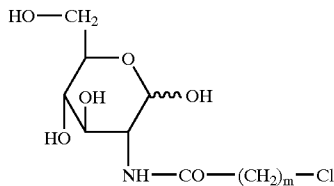
(X)

wherein m is as defined hereinbefore, which is condensed with an amine of formula (XI):

(XI)

wherein R$_1$, R$_2$ and R$_3$ are as defined hereinbefore, to yield a compound of formula (Ia$_4$), which if necessary is purified, and which is optionally separated into its isomers according to a conventional separation technique.

The molecules of formula (Ia$_5$) defined hereinbefore are obtained starting from the compound of formula (XI):

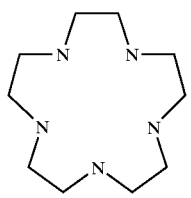
(XII)

which is reacted with a haloalkylammonium halide of formula (XIII):

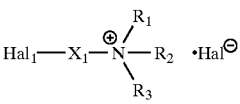
(XIII)

wherein X$_1$, R$_1$, R$_2$ and R$_3$ are as defined hereinbefore, and Hal and Hal$_1$, which may be identical or different, represent halogen atoms, to yield a compound of formula (XIV):

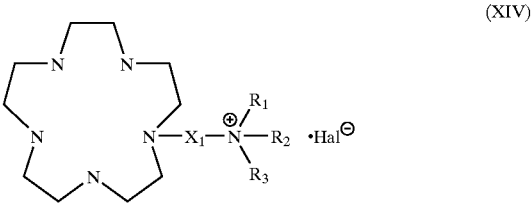
(XIV)

wherein X$_1$, R$_1$, R$_2$, R$_3$ and Hal are as defined hereinbefore, which is reacted with sodium pertechneate in the presence of tin chloride, to yield a compound of formula (Ia$_5$), which if necessary is purified.

The molecules derived from piroxicam of formula (Ib$_1$) defined hereinbefore are obtained starting from piroxicam, which is reacted with a linear or branched (C$_1$–C$_6$)alkyl halide, the resulting compound being purified if necessary.

The molecules of formula (Ib$_2$) defined hereinbefore are obtained starting from the corresponding amine, which is reacted with a linear or branched (C$_1$–C$_6$)akyl halide, the resulting compound being purified if necessary.

In biological studies, the compounds of the present invention have demonstrated an increased tropism for cartilaginous tissues. Those molecules, functionised by the quaternary ammonium function, are furthermore distinguished by pharmaceutical behaviour very different from that of the non-functionalised molecules.

For example, a more elevated concentration has been observed in cartilage up to one hour after administration.

The invention extends also to pharmaceutical compositions comprising as active ingredient at least one compound of formula (I) with one or more appropriate inert, non-toxic excipients. Amongst the pharmaceutical compositions according to the invention there may be mentioned more especially those which are suitable for oral, parenteral (intravenous or subcutaneous) or nasal administration, tablets or dragés, sublingual tablets, gelatin capsules, lozenges, suppositories, creams, ointments, dermal gels, injectable preparations, drinkable suspensions etc.

The useful dosage can be adapted in accordance with the nature and the severity of the disorder, the administration route and the age and weight of the patient and also varies in accordance with the nature of the compound used.

The following Examples illustrate the invention but do not limit it in any way.

The starting materials used are known products or products prepared according to known procedures.

The structures of the compounds described in the Examples were determined according to customary spectroscopic techniques (infra-red NMR, mass spectrometry . . . ).

EXAMPLE 1

{3-{[(Z)-5-Chloro-2,3-dihydro-3-(hydroxy-2-thienylmethylene)-2-oxo-1H-indol-1-yl]carbonylamino}propyl}trimethylammonium chloride Step A: N-[3-(Dimethylamino)propyl]-5-chloro-2,3-dihibydro-2-oxo-1H-indole-1-carboxamide 12.08 mmol of 3-(dimethylamino)propylamine are added at ambient temperature to a solution of 12.08 mmol of 4-nitrophenyl 5-chloro-2,3-dihydro-2-oxo-1H-indole-1-carboxylate in 70 ml of dichloromethane. The reaction is immediate. After extraction of the resulting solution with a 0.05N solution of sodium hydroxide until the aqueous phase no longer exhibits a yellow colour, the organic phase is dried, filtered and evaporated under reduced pressure. The expected compound is isolated in the form of a brown solid.
Melting point: 84–85° C.

Step B: (Z)-N-[3-(Dimethylamlno)propyl]-5-chloro-2,3-dihydro-3(hydroxy-2-thienylmethylene)2-oxo-1H-indole-1-carboxamide hydrochloride Under an argon atmosphere, 2.10 ml of triethylamine and 7.44 mmol of 2-thehoyl chloride are added to a 0° C. solution of 7.44 mmol of the compound obtained in the above Step and 186 mg of 4-N,N-dimethylaminopyridine in 5 ml of dimethylformamide. The reaction mixture is stirred at ambient temperature for 3 hours. Following the addition of 4 ml of methanol then 4 ml of 37% hydrochloric acid, the mixture is stirred at ambient temperature again for 1 hour and subsequently filtered. The yellow solid obtained is washed with ice-cold water and dried, yielding the expected product.
Melting point: 197–198° C. (decomposition)

Step C: (Z)-N-[3-(Dimethylamino)propyl]-5-chloro-2,3-dihydro-3-(hydroxy-2-thienylmethylene)-2-oxo-1H-indole-1-carboxamide sodium salt A suspension containing 2.49 mmol of the product obtained in the above Step and 1.25 mmol of $Na_2CO_3$ in 70 ml of methanol is stirred at ambient temperature for 5 hours. The reaction mixture is then concentrated under reduced pressure and filtered. The precipitate is washed with ice-cold water and dried. The product obtained is treated with $Na_2CO_3$ in methanolic medium at ambient temperature again for 30 minutes. After evaporation, washing the residue with methanol and drying, the expected product is obtained.
Melting point: 211–212° C. (decomposition)

Step D: (Z)-(5-Chloro-1,2-dihydro-2-oxo-1-{[3-(trimethylammonio)propyl]-aminocarbonyl}-3H-indol-3-ylidene) 2-thienylmethanolate 3.33 mmol of methyl iodide are added under an argon atmosphere to a solution of 2.22 mmol of the compound obtained in the above Step in 30 ml of methanol. The mixture is left at ambient temperature for 3 hours. The expected product, which precipitates in the form of a yellow solid as the reaction proceeds, is isolated by filtration, washed with methanol and with ether, and dried.
Melting point: 260–261° C. (decomposition)

Step E: {3-{[(Z)-5-Chloro-2,3-dihydro-3-(hydroxy-2-thienylmethyle)-2-oxo-1H-indol-1-yl]carbonylamino}propyl}trimethylammonium chloride 2.5 ml of 2N ethereal hydrogen chloride are added to a solution of 0.95 1mmol of the product obtained in the above Step in 7 ml of dimethylformamide. The reaction mixture is stirred for 10 minutes at ambient temperature. The solution obtained is subsequently poured into 100 ml of ether. The yellow precipitate obtained is immediately filtered, washed thoroughly with ether and dried.
Melting point: 209–211° C.

EXAMPLE 2

{3-{{4-[bis(2-Chloroethyl)amino]-L-phenylananyl}amino}propyl}-trimethylammonium hydrochloride Step A: 1-{{N-tert-butoxycarbonyl-4-[bis(2-chloroethyl)amino]-L-phenylalanyl}amino}-3-(dimethylamino)propane 2.7 mmol of triethylamine and 1.98 mmol of di-tert-butyl dicarbonate are added in succession, at ambient temperature, to a solution of 1.32 mmol of melphalan hydrochloride in 7 ml of methanol. The mixture is then brought to 30–40° C. As soon as dissolution has taken place, the solution is stirred for 30 minutes at ambient temperature and then evaporated under reduced pressure. The residue obtained is treated with an ice-cold dilute solution of hydrochloric acid (0.01 N) until a pH of 2 is reached. The solution is then immediately extracted with ethyl acetate. The organic phase is subsequently dried, filtered and concentrated under reduced pressure. The intermediate obtained is then taken up in 10 ml of dichloromethane. 1.33 mmol of 1-hydroxybenzotriazole and 1.33 mmol of 3-(dimethylamino)propylamine are added in succession to the resulting solution. A solution of 1.33 mmol of dicyclohexylcarbodiimide in 10 ml of dichloromethane is then added to the mixture obtained. The reaction mixture is stirred at ambient temperature for 5 hours. The urea formed is isolated by filtration. The filtrate is then extracted with a 1N $NaHCO_3$ solution and subsequently washed with water. The organic phase is dried, filtered and evaporated under reduced pressure. The residue obtained is then purified by chromatography on silica gel (eluant: dichloromethane/ethanol, 1/1, then dichloromethane/ethanol/ammonia, 50/49/1). The expected compound is isolated in the form of an oil which crystallises.
Melting point: 80–82° C. (decomposition)

Step B: {3-{{N-tert-butoxyearbonyl-4-[bis(2-chloroethyl)amino]-L-phenyl-alanyl)}amino}propyl}trimethylammonium iodide 0.92 mmol of methyl iodide is added under an inert atmosphere to a solution of 0.61 mmol of the compound described in Step A in 5 ml of ethanol. The reaction mixture is left at ambient temperature for three hours and then concentrated under reduced pressure. The residue obtained is taken up in the minimum amount of methanol and then poured into an ethereal solution. The expected product is isolated in the form of a very hygroscopic solid by means of filtration, washing with ether and drying.
Melting point: 139–142° C.

Step C: {3-{{4-[bis(2-Chloroethyl)amino]-L-phenylalanyl}amino}propyl}trimethylammonium hydrochloride 0.148 mmol of the product obtained in Step B is treated at ambient temperature for two hours with 10 ml of 2N hydrochloric ethanol. The solution is then evaporated under reduced pressure. The residue obtained is dissolved in 50 ml of methanol and passed over resin for a few minutes. The methanolic fractions are evaporated off under reduced pressure. The residue obtained is taken up in the minimum amount of methanol and poured into an ethereal solution. The expected product is isolated in the form of a very hydroscopic white-beige solid by means of filtration, washing with ether and drying.
Melting point: 115–120° C.
Index of rotation: $[\alpha]_D^{25}$=+49.2° (c=1.04%, 1N HCl)

EXAMPLE 3

{3-{{4-[4-[bis(2-Chloroethyl)amino]phenyl]butanoyl}amino}-propyl}-trimethylammonium iodide Step A: N-[3-(Dimethylamino)propyl]-4-{4-[bis(2-chloroethyl)amino]phenyl}-butyramide 1.25 ml of thionyl chloride is added at 0° C., under an inert atmosphere, to a solution of 1.61 mmol of chlorambucil in 5 ml of dichloromethane The reaction mixture is stirred at 4° C. for 16 hours and then excess $SOCl_2$ is evaporated off under reduced pressure. The residue obtained is taken up in 10 ml of dichloromethane. 1.61 mmol of 3-(dimethylamino)

propylamine dissolved in 10 ml of dichloromethane are added to the resulting solution at 0° C. under an inert atmosphere. The mixture is then stirred at ambient temperature for 1 hour. At the end of that time, a second addition of 1.61 mmol of diamine is carried out. After 4 hours+ stirring, the reaction mixture is evaporated under reduced pressure. Following neutralisation with a 1N NaHCO$_3$ solution, the aqueous phase is extracted several times with dichloromethane. The different organic phases are combined, washed with water until neutral, dried, filtered and evaporated under reduced pressure. The residue obtained is purified by chromatography on silica gel (eluant: gradient of ethanol in dichloromethane starting from 0 and going up to 50% and then, to finish, the eluant: dichloromethane/ethanol/ammonia, 50/49/1, is used). The expected product is obtained in the form of an oil.

Step B: {3-{{4-[4-[bis(2-Chloroethyl)amino]phenyl]butanoyl}amino}propyl-trimethylammonium iodide 1.01 mmol of methyl iodide is added under an inert atmosphere to a solution of 1.34 mmol of the compound obtained in the above Step in 7 ml of ethanol. The mixture is stirred at ambient temperature for 3 hours and then evaporated under reduced pressure. The oil obtained is taken up in the minimum amount of methanol. The resulting solution is then poured into 150 ml of ether and stirred at 0° C. for 1 hour. The precipitate formed is subsequently filtered off. After washing with ether and drying, the expected product is obtained in the form of a very hygroscopic beige solid.

Melting point: 118–120° C. (decomposition)

EXAMPLE 4

2-(N,N,N-trimethylammonioacetamido)-2-deoxy-α,β-D-glucopyranose chloride

Step A: 2-Chloroacetamido-2-deoxy-α,β-D-glucupyranose 46.4 mmol of chloroethanoyl chloride are added dropwise to a solution, cooled to 0° C., of 23.2 mmol of glucosamine hydrochloride and 40 mmol of K$_2$CO$_3$ in 40 ml of distilled water. The whole is stirred for 1 hour. After evaporation of the aqueous solution under reduced pressure, the solid obtained is washed several times with ethanol. The ethanolic phase is then concentrated under reduced pressure until precipitation of white solid occurs. After having been sufficiently cooled to 0° C., the solution is filtered. The white solid obtained is triturated with acetone and dried, yielding the expected product after recrystallisation from ethanol.

Melting point: 183–185° C.

Step B: 2(N,N,N-Trimethylammonioacetamido)-2-deoxy-α,β-D-glucopyranose chloride 9.8 mmol of the compound obtained in the above Step and 10 ml of a 4M ethanolic solution of triethylamine are placed under an inert atmosphere for 3 days at 40° C. The expected product is obtained by filtration of the precipitate formed, followed by washing with ethanol, with ether and drying.

Meltin point: 240–242° C.

EXAMPLE 5

2-(Pyridinioacetamido)-2-deoxy-α,β-D-glucopyranese chloride 9.8 mmol of the compound obtained in Step A of Example 4 are placed under an inert atmosphere in 50 ml of pyridine for 3 days at 40° C. The pyridine is then evaporated off in vacuo and the expected product is obtained by washing with ethanol, with ether and drying.

Melting point: 223–225° C.

EXAMPLE 6

{3-[(4-Hydroxy-2-methyl-1,1-dioxide-2H-1,2-benzothiazin-3-yl)-carboxamido]propyl}trimethylammonium iodide 3.39 mol of N-[3-(dimethylamino)propyl]-4-hydroxy-2-methyl-1,1-dioxo-2H-1,2-benzo-thiazin-3-yl]carboxamide are heated for 24 hours at 80° C. under argon in the presence of 3 ml of iodomethane. After cooling, the precipitate obtained is filtered, washed with acetone and dried to yield the expected product.

Melting point: 220–222° C. (decomposition)

EXAMPLE 7

2-[(4-Hydroxy-2-methyl-1,1-dioxo-2H-1,2-benzothiazin-3-yl)-carboxaniido]-N-methylpyridinium iodide The expected product is obtained by reaction of piroxicam with pyridine in accordance with the process described in Example 6.

EXAMPLE 8

[15]ane-N5-(N-3-propyl)triethylammonium bromide hydrochloride labelled with technetium

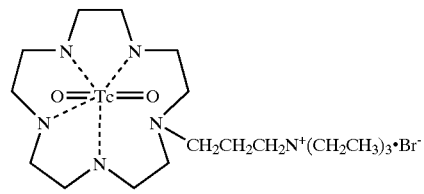

Step A: [15]ane-N5-(N-3-propyl)triethylammonium bromide hydrochloride 10 mmol of (3-bromopropyl)triethylammonium bromide are added to 10 mmol of [15ane]-N5$^{(*)}$ dissolved in 50 ml of deionised water. After heating at 90° C. for 12 hours under an inert atmosphere, the water is evaporated off. The oily residue is washed twice with dichloromethane and then dissolved in 100 ml of ethanol. Treatment with 4 ml of 10N HCl added dropwise, while cooling the balloon flask to 0° C., yields a flaky white precipitate which is filtered, washed with alcohol and then with ether and dried, yielding the expected product.

Melting point: >200° C. (decomposition)

(*)[15ane]-N5:

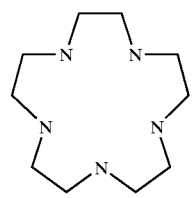

Step B: [15]ane-N5-(N-3-propyl)triethylammonium bromide hydrochloride labelled with technetium Labelling the compound obtained in Step A with technetium is carried out in vacuo in a sterile flask of 15 ml capacity into which the following are introduced:

a solution of 7.5 mmol of the product obtained in Step A in 1 ml of physiological serum, sodium pertechnetate ($^{99m}$TcO$_4^-$, 25 mCi; 925 MBq) dissolved in 1 ml of physiological serum; the flask is heated at 85° C. for 5 minutes (metal bath), a deoxygenated aqueous solution of SnCl$_2$.2H$_2$O (9 mmol), prepared for immediate use. The labelling is carried out by heating for 30 minutes at 85° C.

PHARMACOLOGICAL STUDY OF THE COMPOUNDS OF THE INVENTION

Pharmacokinetic Study: Tissue Distribution Study

This study was carried out with molecules labelled with $^{14}C$. The tissue distribution study was carried out by direct measurement of the radioactivity across whole-body sections in accordance with the following method: male Sprague-Dawley rats were administered intravenously or orally with a dose of the labelled molecule. Then, at times raging from 5 minutes to 24 hours after the administration, the animals were sacrificed by ether inhalation and frozen in liquid nitrogen.

Sections were then prepared using a cryomicrotome and, after desiccation, the distribution of radioactivity was measured using an image analyser.

The results obtained with the compounds of the invention demonstrate that the compounds exhibit an increased tropism for cartilaginous tissues.

In respect of the compounds of Examples 4 and 5, apart from the kidney, an elimination organ which binds significant amounts of radioactivity in the first minutes following the injection, cartilage, and to a lesser degree skin, are the only targets. When the same study is carried out with non-functionalised glucosamine, the liver is the main target organ.

In respect of the compound of Example 6, cartilage exhibits a far greater affinity than the surrounding tissues. Maximum binding is achieved 5 minutes after injection. A very high affinity for cartilage is likewise observed when this study is performed after administration of the labelled molecule by the oral route.

As for the compound of example 8, that compound has a raised concentration in cartilaginous tissue 10 minutes after injection.

What is claimed is:

1. A compound selected from those represented by formula (Ib2):

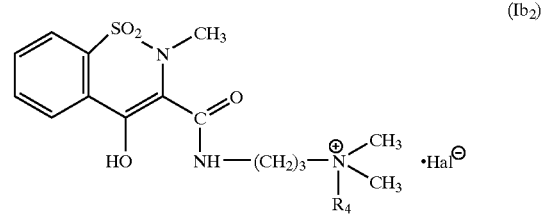

wherein:

$R_4$ represents a linear or branched $(C_1-C_6)$alkyl group, and

Hal represents a halogen atom.

2. A pharmaceutical composition comprising as active ingredient a compound according to claim 1, in combination with one or more pharmaceutically acceptable, inert, non-toxic excipients or carriers.

3. A method of treating a living body afflicted with pathologies caused by attack on cartilage selected from arthritis, osteoarthritis and chondrosarcomas, comprising administering to the living body an amount of a compound of claim 1 which is effective for treatment of the pathology.

* * * * *